United States Patent [19]

Drent

[11] Patent Number: 4,664,851
[45] Date of Patent: May 12, 1987

[54] PROCESS FOR THE CO-PRODUCTION OF CARBOXYLIC ACIDS AND CARBOXYLIC ACID ESTERS

[75] Inventor: Eit Drent, Amsterdam, Netherlands

[73] Assignee: Shell Oil Company, Houston, Tex.

[21] Appl. No.: 399,163

[22] Filed: Jul. 19, 1982

[30] Foreign Application Priority Data

Dec. 30, 1981 [GB] United Kingdom ............ 8139072

[51] Int. Cl.$^4$ .................. C11C 3/02; C07C 51/12; C07C 67/37; C07C 67/36
[52] U.S. Cl. .................. 260/410.9 R; 260/408; 260/410.5; 260/413; 260/546; 260/549; 560/51; 560/55; 560/64; 560/111; 560/103; 560/105; 560/106; 560/112; 560/114; 560/175; 560/179; 560/187; 560/234; 560/73; 562/406; 562/497; 562/517
[58] Field of Search ............ 560/232, 265, 103, 130, 560/105, 106, 111, 112, 114, 175, 179, 187, 186, 51, 55, 64, 73, 226, 227; 562/517, 406, 497; 260/413, 408, 410.9 R, 410.5

[56] References Cited
U.S. PATENT DOCUMENTS 4,189,441 2/1980 Braca et al. ............ 560/232
4,241,219 12/1980 Wan .................. 560/232

OTHER PUBLICATIONS

Merck Index, 9th ed., Merck & Co. Inc., Rahway, N.J. 1976, p. 226, #1782.

Primary Examiner—Werren B. Lone
Attorney, Agent, or Firm—Ronald R. Reper

[57] ABSTRACT

Process for the co-production of carboxylic acids of the general formula $R^1$—COOH and $R^2$—COOH and carboxylic acid esters of the general formula $R^1$—COOCH$_2$R$^2$ and $R^2$—COOCH$_2$R$^1$ from carboxylic acid esters of the general formula $R^1$—COOR$^2$ and/or ethers of the general formula $R^3$OR$^4$ ($R^1$, $R^2$, $R^3$, $R^4$ representing (substituted) alkyl or (substituted) aryl, alkaryl or aralkyl, $R^1$ also representing H), carbon monoxide and hydrogen at elevated temperature and pressure in the presence of a ruthenium compound, a further Group VIII metal compound, and a compound $R^5$Hal or $R^5$COHal where $R^5$ has one of the meanings given for $R^2$ and Hal is iodine or bromine, the reaction mixture being substantially free from other transistion metal or Group II metal iodides or bromides, and containing a trivalent nitrogen compound containing a group

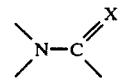

(X=O or S), such as an amide, a carbamate, a urea or a derivative thereof. The process is of special interest for the selective conversion of methyl acetate into ethyl acetate and acetic acid at pressures well below 100 bar.

19 Claims, No Drawings

PROCESS FOR THE CO-PRODUCTION OF CARBOXYLIC ACIDS AND CARBOXYLIC ACID ESTERS

FIELD OF THE INVENTION

This invention relates to a process for the co-production of carboxylic acids and carboxylic esters from carboxylic acid esters or ethers, carbon monoxide and hydrogen in the presence of a homologation catalyst system.

BACKGROUND OF THE INVENTION

The production of carboxylic acid esters via homologation has already been described in the literature. It is known from European Patent Application No. 31606 that the stoichiometry of the known reactions of methyl acetate with carbon monoxide and hydrogen can be altered most advantageously to produce one mole of ethyl acetate and two moles of acetic acid from two moles of methyl acetate. The catalytic system comprises three metal compounds: a ruthenium compound, a further Group VIII metal compound, and a bromide or iodide of a Group II or transition metal, preferably in the presence of a promoter, typically an amine or a phosphine.

It has been described and claimed in our co-pending application Ser. No. 395,946, filed July 7, 1982 (K-0478), now abandoned, that an alkyl or acyl iodide or bromide can replace the Group II or transition metal iodide or bromide in the catalytic system as disclosed in European Patent Application No. 31606, provided that the quantity of amine in the reaction mixture does not exceed a certain rather low level.

SUMMARY OF THE INVENTION

The present invention relates to a process for the co-production of carboxylic acids and carboxylic acid esters from carboxylic acid esters having one carbon atom less in the molecule, carbon monoxide and hydrogen in the presence of a catalytic system. The invention relates in particular to a process for the co-production of acetic acid and ethyl acetate from methyl acetate under mild process conditions. Carboxylic acid esters produced according to the process according to the present invention are thus homologs of the carboxylic acid esters used as starting materials.

It has been found that another class of trivalent nitrogen compounds, i.e. trivalent nitrogen compounds containing a group

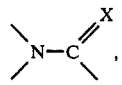

wherein X is O or S, can also be applied advantageously in the process for the coproduction of carboxylic acids and carboxylic acid esters using a catalytic system based on a ruthenium compound, a further Group VIII metal compound and an alkyl or acyl iodide or bromide.

DESCRIPTION OF THE PREFERRED EMBODIMENTS

The present invention provides a process for the co-production of carboxylic acids of the general formula $R^1$—COOH and $R^2$—COOH and carboxylic acid esters of the general formula $R^1$—COOCH$_2R^2$ and $R^2$—COOCH$_2R^1$ wherein each of the groups $R^1$ and $R^2$, which may be the same or different, represents an alkyl group having from 1 to 20 carbon atoms which may be substituted by one or more inert substituents such as fluorine or chlorine-containing moieties or hydroxy, alkoxy or alkanoyl groups, or an aryl, alkaryl or aralkyl group having upto about 20 carbon atoms which may be substituted by one or more inert substituents such as fluorine or chlorine-containing moieties or alkoxy or alkanoyl groups, while $R^1$ may also represent a hydrogen atom, wherein a carboxylic acid ester of the general formula $R^1$—COOR$^2$ and/or an ether of the general formula $R^3OR^4$, wherein $R^1$ and $R^2$ are as defined hereinbefore and each of $R^3$ and $R^4$, which may be the same or different, represents an alkyl group having from 1 to 20 carbon atoms which may be substituted by one or more inert substituents such as fluorine or chlorine-containing moieties or hydroxy, alkoxy or alkanoyl groups, or an aryl, alkaryl or aralkyl group having up to about 20 carbon atoms which may be substituted by one or more inert substituents such as fluorine or chlorine-containing moieties or alkoxy or alkanoyl groups, is reacted with carbon monoxide and hydrogen at elevated temperature and pressure in the presence of a catalytic system which comprises a ruthenium compound, a further Group VIII metal compound, and a compound of the general formula $R^5$Hal or $R^5$COHal where $R^5$ has one of the meanings given above for $R^2$ and Hal, represents an iodine or bromine atom, the reaction mixture being substantially free from other transition metal or Group II metal iodides or bromides, and containing a trivalent nitrogen compound containing a group

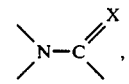

wherein X represents an oxygen or sulfur moiety.

It should be noted that the composition of the reaction product mixture will be governed by the choice of the starting carboxylic acid esters and/or ethers. For instance, when starting materials are used wherein the groups $R^1$ and $R^2$ are identical, such as in methyl acetate, dimethyl ether and ethyl propionate, the reaction product mixture will normally contain only the carboxylic acid ester homolog and the appropriate acid. When starting materials are used wherein the groups $R^1$ and $R^2$ are not identical, a more complex reaction product mixture will be obtained which comprises normally at least two carboxylic acid ester homologs and two appropriate carboxylic acids. For instance, when ethyl acetate is used as the starting material, the reaction product mixture comprises propyl acetate, ethyl propionate, propionic acid and acetic acid.

It will be appreciated that any carboxylic acid ester homolog produced according to the present process can serve as starting material in the process according to the present invention, thus forming the next carboxylic acid ester homolog(s) and the appropriate carboxylic acid(s). In addition, since carboxylic acids are produced in the process according to the present invention, transesterification reactions, i.e. reactions between carboxylic acids and carboxylic acid esters, or between different carboxylic acid esters, may also occur under the prevailing reaction conditions. It will be clear that transesterification reactions do not alter the product composition when the starting material comprises compounds wherein $R^1$ and $R^2$ are identical, but may alter the product composition when the groups $R^1$ and $R^2$ are not identical.

For the purpose of the present invention, carboxylic acids and carboxylic acid esters, obtained via a further homologation of produced carboxylic acid ester, or obtained by a transesterification process under the prevailing conditions, are considered to be within the scope of the present invention.

From the above it will be clear that preference is given to processes wherein starting materials are used wherein the groups $R^1$ and $R^2$ are identical since a less complex reaction mixture will be obtained. The process according to the present invention is of special interest for the coproduction of acetic acid and ethyl acetate from methyl acetate according to the equation: $2 CH_3COOCH_3 + 2 CO + 2 H_2 \rightarrow CH_3COOC_2H_5 + 2 CH_3COOH$, since the products can be obtained with high selectivity and close to the stoichiometrically expected ratio. This is of special interest when the process according to the invention is part of an integrated process, wherein acid produced—for instance, acetic acid—is to be recycled in the process. Moreover, the process according to the present invention can be carried out conveniently at surprisingly low pressures, e.g. pressures well below 100 bar can be used advantageously.

Suitable starting materials which can be used conveniently in the process according to the present invention include compounds of the general formula $R^1$—$COOR^2$ and/or $R^3OR^4$, wherein each of $R^1$, $R^2$, $R^3$ and $R^4$, which may be the same or different, represents an alkyl group having from 1 to about 12 carbon atoms, or an aryl, alkaryl or aralkyl group having up to about 12 carbon atoms, while $R^1$ may also represent a hydrogen atom. Preference is given to the use of compounds of the general formula $R^1$—$COOR^2$ and/or $R^3OR^4$, wherein $R^1$, $R^2$, $R^3$ and $R^4$ are the same, and each represents an alkyl group having from 1 to about 12 carbon atoms or an aryl, alkaryl or aralkyl group having up to about 12 carbon atoms. Most preferred starting materials are methyl acetate and dimethyl ether.

When ethers of the general formula $R^3OR^4$ are used as starting materials in the process according to the present invention, it would appear that these compounds will be converted primarily into the corresponding esters by the introduction of a carbon monoxide moiety into the molecule, which molecule may then undergo the homologation reaction according to the present invention. If desired, the reaction according to the present invention may be carried out in two stages when an ether is used as the starting material. Firstly, the ether is converted into the corresponding ester which in its turn, in the same or in a different vessel, is converted into the final products. If desired, mixtures of carboxylic acid esters and/or ethers can be used as starting materials.

Ruthenium compounds which can be used conveniently in the process according to the present invention include ruthenium(III) chloride, ruthenium(III) chloride trihydrate, ruthenium(IV) chloride, ruthenium(III) bromide, the ruthenium oxides, organic ruthenium salts such as ruthenium(III) propionate, ruthenium(III) butyrate, ruthenium pentacarbonyl, trirutheniumdodecacarbonyl and mixed ruthenium halocarbonyls such as bis-(rutheniumtricarbonyl-dibromide), and other organoruthenium complexes.

Further Group VIII metal compounds which can be used together with a ruthenium compound in the catalytic system include palladium and, especially, rhodium compounds, although other Group VIII metal compounds can also be used. Examples of suitable rhodium compounds include rhodium oxide, rhodium(III) hydroxide, rhodium(III) chloride, rhodium(III) chloride trihydrate, rhodium(III) bromide, rhodium(III) iodide and the corresponding pyridine and phosphine complexes such as tris(pyridine) rhodium(III) chloride or dichloro bis-(triphenylphosphine) rhodium, rhodium(III) formate, rhodium(III) acetate, rhodium(III) butyrate, rhodium(III) naphthenate, dirhodium octacarbonyl, tetrarhodium dodecacarbonyl, hexarhodium hexadecacarbonyl, rhodium dicarbonylacetylacetonate and other organo-rhodium complexes. Preference is given to the use of rhodium(III) chloride trihydrate.

Examples of suitable palladium compounds include palladium chloride, palladium chloride dihydrate, palladium bromide, palladium iodide, palladium oxide, or an organic palladium salt or complex such as palladium formate, palladium acetate, palladium butyrate and palladium acetylacetonate. Preferred palladium compounds are palladium chloride, palladium chloride dihydrate and palladium acetate.

The molar ratio of ruthenium compound to further Group VIII metal compound is not critical and can vary between wide limits, e.g. atomic ratios of ruthenium to further Group VIII metal between about 50:1 and about 1:20, especially between about 10:1 and 1:5, are suitable.

The amount of ruthenium compound and further Group VIII metal compound to be used is not critical, and any amount which exerts catalytic activity can be used. Amounts as low as about 0.001% w, calculated on carboxylic acid ester or ether to be converted can be used, preference being given to amounts in the range of from about 0.01–10% w, most preferably between about 0.05–5% w.

Any iodide or bromide $R^5Hal$ or $R^5COHal$ may be used in the process according to the present invention, but preferably $R^5$ has one of the preferred meanings given above for $R^2$, and preferably the group $R^5$ is identical to one of the groups $R^1$, $R^2$, $R^3$ or $R^4$ in the starting material, as this avoids the formation of additional mixed products. Especially preferred is the use of a reaction mixture in which $R^1$ and $R^2$ are the same, and the iodide or bromide has the formula $R^2I$, $R^2Br$, $R^2COI$ or $R^2COBr$. Thus, for example, when using the preferred feedstocks methyl acetate and/or dimethyl ether, methyl iodide or bromide or acetyl iodide or bromide, or any mixture thereof, is preferably used.

The quantity of iodide or bromide added to the reaction mixture is not crucial. Suitably, the number of moles of added iodide plus bromide per gram atom of total group VIII metal is in the range of from about 0.1:1 to about 200:1, preferably from about 1:1 to about 100:1, and especially from about 10:1 to about 50:1.

As stated hereinbefore, the process according to the present invention is carried out in the presence of a trivalent nitrogen compound containing a group

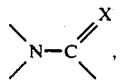

wherein X is O or S.

Examples of trivalent nitrogen compounds which can be used suitably in the process according to the present invention comprise amides which can be represented by the general formula:

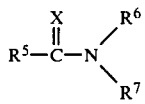 (I)

wherein $R^5$ represents an alkyl, cycloalkyl, aryl, alkaryl or aralkyl group; $R^6$ and $R^7$, which may be the same or different, each represents a hydrogen atom or an alkyl, aryl, alkaryl or aralkyl group, which may also contain a

moiety, or $R^6$ and $R^7$ form a cyclic structure together with the nitrogen atom to which they are attached, which structure may contain one or more nitrogen or oxygen atoms, or one of $R^6$ and $R^7$ may form a cyclic structure with $R^5$; and X represents an oxygen or sulfur moiety.

Examples of amides comprise compounds according to the general formula I, wherein $R^5$ represents an alkyl group of up to 8 carbon atoms; $R^6$ and $R^7$, which may be the same or different, each represents a hydrogen atom or an alkyl or aryl group of up to 8 carbon atoms and X is O or S, such as acetamide, N-methyl acetamide, N,N-dimethyl acetamide, N-ethyl acetamide, N,N-dimethyl cyclohexyl carboxamide, N,N-dimethyl benzamide, N,N-diethyl benzamide, N-phenyl acetamide, N,N-diphenyl acetamide, N-methyl-N-phenyl acetamide, N-formyl morpholine, N-acetyl morpholine, N-formyl piperidine, N-acetyl piperidine, N-acetyl-N'-methyl piperazine, N-methyl pyrrolidone and the corresponding thioderivatives. Preference is given to the use of N,N-dialkyl amides, in particular to N,N-dimethyl acetamide.

Suitably, the reaction mixture does not contain more than about 1 mol amide per gram atom of ruthenium, and preferably not more than about 0.5 mol amide, in particular between about 0.05 and about 0.5 mol amide per gram atom of ruthenium.

Although the use of an amide in an amide/ruthenium ratio above 1 does still lead to the production of homologs, it appears that other products are being formed with a rapidly increasing rate, acetic acid anhydride and ethylidene diacetate becoming the predominant (by)-products.

Compounds according to the general formula I also include diamides and triamides such as diacetamide, triacetamide, dibenzamide, tribenzamide and N-methyl dibenzamide as well as imines such as succinimide, 1,2-cyclohexane dicarboxamide and N-phenyl phthalimide.

Examples of trivalent organic nitrogen compounds which can also be used suitably in the process according to the present invention comprises carbamates which can be represented by the general formula:

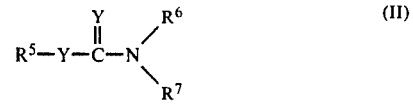 (II)

wherein $R^5$, $R^6$, $R^7$ and X are as defined hereinbefore and Y represents an oxygen or sulfur moiety.

Examples of carbamates comprise compounds according to the general formula II wherein $R^5$ represents an alkyl group of up to 8 carbon atoms; $R^6$ and $R^7$, which may be the same or different, each represents a hydrogen atom, an alkyl or aryl group of up to 8 carbon atoms and X and Y each represents an oxygen or sulfur moiety, such as the alkyl and aryl esters of carbamic acid, e.g. methyl carbamate, ethyl carbamate and phenyl carbamate, N-methyl methyl carbamate, N-ethyl methyl carbamate, N-phenyl methyl carbamate, N-methyl ethyl carbamate, N-ethyl ethyl carbamate, N-phenyl ethyl carbamate, N-methyl phenyl carbamate, N-ethyl phenyl carbamate, N-phenyl phenyl carbamate, N,N-dimethyl methyl carbamate, N,N-diethyl methyl carbamate, N,N-diphenyl methyl carbamate, N,N-dimethyl ethyl carbamate, N,N-diethyl ethyl carbamate, N,N-diphenyl ethyl carbamate, N,N-dimethyl phenyl carbamate, N,N-diethyl phenyl carbamate, N,N-diphenyl phenyl carbamate, N-methyl-N-ethyl methyl carbamate, N-methyl-N-ethyl ethyl carbamate and the corresponding thiocarbamates. Preference is given to the use of N-phenyl carbamates, in particular to N-phenyl alkyl carbamates such as N-phenyl methyl carbamate and N-phenyl ethyl carbamate.

The compounds according to the general formula II are present in the reaction mixture in catalytic quantities, but the precise amount appears not to be very critical. Suitably, the molar ratio of a compound according to the general formula II to ruthenium is in the range of from about 0.01 to about 1.5, preferably in the range of from about 0.05 to about 0.5.

Further examples of trivalent nitrogen compounds having the group

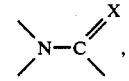

comprise urea and derivatives thereof, i.e. compounds according to the genera formula:

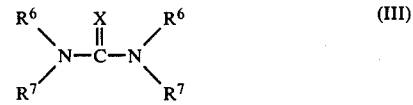 (III)

wherein $R^6$, $R^7$ and X are as defined hereinbefore. Examples of compounds according to the general formula III comprise urea, thiourea, 1,3-disubstituted ureas such as 1,3-dimethyl urea, 1,3-diethyl urea and 1,3-diphenyl urea, 1,1-dimethyl urea, 1,1-diphenyl urea and 1,1,3,3-tetramethyl urea. Suitably, the molar ratio of a compound according to the general formula III to ruthenium is in the range of from about 0.01 to about 1.5, preferably in the range of from about 0.05 to about 0.5.

The process according to the present invention can be carried out using a wide range of temperatures. Temperatures up to about 300° C. can be suitably applied. Preference is given to temperatures in the range of from about 50° C. to about 200° C., most preferred temperatures are in the range between about 125° C. and about 175° C.

The process according to the present invention can be carried out using low pressures, e.g. pressures as low as about 5 bar. Pressures in the range of from about 20 to about 100 bar are preferred. Higher pressures, e.g. pressures as high as about 1000 bar can be applied, but they are generally not economical because of the investment and energy costs involved.

According to the reaction equation, carbon monoxide and hydrogen are consumed in a molar ratio of 1:1. It has been found, however, that without any substantial disadvantage wider molar ratios, e.g. ratios of from about 1:10 to about 10:1 can be applied. Preference is given to ratios carbon monoxide:hydrogen in the range of from about 1:0.5 to about 1:3.

The process according to the present invention may be carried out in the presence of a solvent. Suitable solvents include carboxylic acids such as acetic acid or propanoic acid; carboxylic acid esters, such as methyl acetate, ethyl acetate, methyl propionate or ethyl propionate (being used as solvent as well as starting material); and cyclic ethers such as tetrahydrofuran, 1,4-dioxane, 1,3-dioxane and the dioxolanes. Also, dialkyl ethers used in excess as starting material may be regarded as solvent for the process according to the present invention. Suitable dialkyl ethers include dimethyl ether, diethyl ether and methyl t-butyl ether.

Other compounds which can be used as solvent in the process according to the present invention include sulphones and sulphoxides. Examples of such compounds are dimethylsulphone, sulpholane, 2-methyl sulpholane, 3-methyl sulpholane, dimethylsulphoxide and diethyl sulphoxide.

Especially good results are obtained when alkanoic acids such as acetic acid are used as solvent. If, however, a solvent other than an alkanoic acid is used, it may be desirable to carry out the reaction in the presence of small amounts of a strong acid. For example, amounts of strong acid of up to about 100 equivalents of acid per gram atom of total Group VIII metal, may be added. Suitable strong acids include those which in aqueous solution at 20° C. have a pKa of less than 3.5, for example, organic acids such as p-toluene sulphonic acid or trifluoromethane sulphonic acid, or mineral acids such as hydrochloric, sulphuric or perchloric acid.

The mild conditions according to the present invention even tolerate the presence of some water in the reaction medium. Although the presence of water is not preferred, amounts of up to about 15% w, based on total solvent, can be present.

The process according to the present invention can be carried out in the liquid phase or in the gaseous phase. Preference is given to a liquid phase which enables a convenient introduction of carbon monoxide and hydrogen into the reaction vessel. If desired, the carbon monoxide and hydrogen can be introduced together into the reaction vessel. The process according to the present invention can be carried out batchwise, semicontinuously or continuously.

The process according to the present invention is also of interest in that it can be integrated with known processes, either for the production of the starting materials (i.e. carboxylic acid esters or the corresponding ethers) or for the conversion of the carboxylic acid esters produced into other products, e.g. by transesterification processes. For instance, when the present process produces ethyl acetate, it can be integrated with a process for the preparation of methyl acetate from acetic acid and methanol using an acidic catalyst. Since the present process produces acetic acid, that compound may be recycled to serve as feedstock for the preparation of methyl acetate. If desired, the present process can also be integrated with a transesterification process, wherein ethyl acetate is transesterified with methanol to give methyl acetate (which can be recycled to serve as feedstock for the present process) and ethanol which can either be sold as such or converted into other products such as ethylene. In such a case acetic acid and/or methyl acetate can be removed from the system in an amount equimolar with ethanol produced.

The following Examples are provided to illustrate the invention and are not to be construed as limiting the invention.

EXAMPLE 1

The experiment was carried out in a 300 ml magnet-driven autoclave of Hastelloy C (trademark) which contained 25 ml methyl acetate, 25 ml acetic acid, 60 mmol methyl iodide, 0.25 mmol rhodium(III) chloride trihydrate, 1 mmol ruthenium(III) chloride trihydrate and 0.3 mmol N,N-dimethyl acetamide. The vessel was pressurized with carbon monoxide (20 bar partial pressure) and hydrogen (40 bar initial pressure). The autoclave was then heated to 160° C. and kept at this temperature for 5 hours, during which time the pressure was maintained constant by feeding in carbon monoxide and hydrogen (1:1), as required. After this time the reaction mixture was analyzed by gas-liquid chromatography and shown to contain 13.0% w ethyl acetate. On a molar basis the conversion of the starting material was about 50%, with an almost 100% selectivity towards the two products, ethyl acetate and acetic acid. Only traces (less than 0.5%) of by-products were detected; in particular, no alcohols were detected.

EXAMPLE 2

The experiment described in Example 1 was repeated using 0.5 mmol rhodium(III) chloride trihydrate and 0.3 mmol N-phenyl ethyl carbamate instead of N,N-dimethyl acetamide. After the reaction the mixture was analyzed by gas-liquid chromatography and shown to contain 16.3% w ethyl acetate. On a molar basis the conversion of the starting material was 65%, with an almost 100% selectivity towards the two products ethyl acetate and acetic acid. Only traces (less than 0.5%) of by-product were detected.

I claim:

1. A process for the co-production of carboxylic acids of the general formula $R^1$—COOH and $R^2$—COOH, and carboxylic acid esters of the general formula $R^1$—COOCH$_2R^2$ and $R^2$—COOCH$_2R^1$ wherein each of the groups $R^1$ and $R^2$, which may be the same or different, represents an alkyl group having from 1 to about 20 carbon atoms or an aryl, or aralkyl group, and $R^1$ may also represent a hydrogen atom, characterized in that a carboxylic acid ester of the general formula $R^1$—COOR$^2$ and/or an ether of the general formula $R^3OR^4$, wherein $R^1$ and $R^2$ are as defined hereinbefore and each of $R^3$ and $R^4$ which may be the same of different, represents an alkyl group having from 1 to about 20 carbon atoms, or an aryl, or aralkyl group, is reacted with carbon monoxide and hydrogen at a temperature of up to about 300° C. and a pressure of up to about 1000 bar in the presence of a catalyst system which comprises a ruthenium compound, a further Group VIII metal compound, and a compound of the general formula $R^5$Hal or $R^5$COHal where $R^5$ has one of the meanings given for $R^2$ and Hal represents an iodine or bromine atom, the reaction mixture being substantially free from other transition metal or Group II metal iodides or bromides, and containing a trivalent nitrogen compound selected from the group of carbamates represented by the general formula:

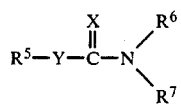   II wherein $R^5$ represents an alkyl, cycloalkyl, aryl, or aralkyl group of up to 8 carbon atoms; $R^6$ and $R^7$, which may be the same or different, each represents a hydrogen atom or an alkyl, aryl, or aralkyl group having up to 8 carbon atoms and which may also contain a

moiety, and X and Y each represents an oxygen or sulfur moiety.

2. The process according to claim 1 characterized in that as starting materials are used compounds of the general formula $R^1$—COOR$^2$ and/or $R^3$OR$^4$, wherein each of $R^1$, $R^2$, $R^3$ and $R^4$, which may be the same or different, represents an alkyl group having from 1 to about 12 carbon atoms or an aryl, or aralkyl group having up to about 12 carbon atoms, and $R^1$ may also represent a hydrogen atom.

3. The process according to claims 1 or 2 wherein the ruthenium compound is selected from the group consisting of rhuthenium (III) chloride, ruthenium(III) chloride trihydrate, ruthenium(IV) chloride, ruthenium(III) bromide, ruthenium oxide, or mixtures thereof.

4. The process according to claims 1 or 2 wherein the further Group VIII metal compound is a rhodium compound.

5. The process according to claims 1 or 2 wherein the further Group VIII metal compound is selected from the group consisting of rhodium oxide, rhodium(III) hydroxide, rhodium(III) chloride, rhodium(III) chloride trihydrate, rhodium(III) bromide, rhodium(III) iodide or mixtures thereof.

6. The process according to claims 1 or 2 wherein the further Group VIII metal compound is rhodium(III) chloride trihydrate.

7. The process according to claims 1 or 2 wherein the further Group VIII metal compound is selected from the group consisting of a palladium compound such as palladium chloride, palladium chloride dihydrate, palladium bromide, palladium iodide, palladium oxide, or mixtures thereof.

8. The process according to claims 1 or 2 wherein the further Group VIII metal compound is selected from the group consisting of palladium chloride, palladium chloride dihydrate, palladium acetate or mixtures thereof.

9. The process according to claims 1 or 2 wherein the ruthenium compound and the further Group VIII metal compound are used in a ratio between about 50:1 and about 1:20.

10. The process according to claims 1 or 2 wherein the ruthenium compound and the further Group VIII metal compound are used in a ratio between about 10:1 and about 1:5.

11. The process according to claims 1 or 2 wherein the group $R^5$ is identical to one of the groups $R^2$, $R^3$ or $R^4$ in the starting material.

12. The process according to claim 1 wherein carbamates according to the general formula II wherein $R^5$ represents an alkyl group of up to 8 carbon atoms; $R^6$ and $R^7$, which may be the same or different, each represents a hydrogen atom or an alkyl or aryl group of up to 8 carbon atoms; and X and Y each represents an oxygen or sulfur moiety are employed.

13. The process according to claim 1 wherein the carbamates are N-phenyl alkyl carbamates.

14. The process according to claim 13 wherein the carbamates are N-phenyl methyl carbamates or N-phenyl ethyl carbamates.

15. The process according to claims 1, 2, 12, 13, or 14 wherein the trivalent nitrogen compound is present in the reaction mixture in an amount in the range of from about 0.05 to about 0.5 mole per gram atom of ruthenium.

16. The process according to claims 1 or 2 wherein the reaction is carried out at a temperature in the range of from about 50° C. to about 200° C.

17. The process according to claims 1 or 2 wherein the reaction is carried out at a temperature in the range of from about 125° C. to about 175° C.

18. The process according to claims 1 or 2 wherein the process is carried out at a pressure between about 20 and about 100 bar.

19. The process according to claims 1 or 2 wherein an alkanoic acid is used as a solvent.

* * * * *